(12) United States Patent
Magnes et al.

(10) Patent No.: US 10,587,022 B2
(45) Date of Patent: Mar. 10, 2020

(54) ADDITIVE FOR A FLOW BATTERY

(71) Applicant: BROMINE COMPOUNDS LTD., Beer Sheva (IL)

(72) Inventors: Ben-Zion Magnes, Meitar (IL); Ran Elazari, Beer-Sheva (IL); Iris Ben-David, Ashdod (IL); Eli Lancry, Gan-Yavne (IL)

(73) Assignee: BROMINE COMPOUNDS LTD., Be'er-Sheva (IL)

( * ) Notice: Subject to any disclaimer, the term of this patent is extended or adjusted under 35 U.S.C. 154(b) by 17 days.

(21) Appl. No.: 15/572,935

(22) PCT Filed: May 9, 2016

(86) PCT No.: PCT/IL2016/050490
§ 371 (c)(1),
(2) Date: Nov. 9, 2017

(87) PCT Pub. No.: WO2016/181389
PCT Pub. Date: Nov. 17, 2016

(65) Prior Publication Data
US 2018/0138568 A1    May 17, 2018

Related U.S. Application Data

(60) Provisional application No. 62/159,395, filed on May 11, 2015, provisional application No. 62/253,148, filed on Nov. 10, 2015.

(51) Int. Cl.
*H01M 10/056* (2010.01)
*H01M 12/08* (2006.01)
(Continued)

(52) U.S. Cl.
CPC ........ *H01M 12/085* (2013.01); *C07D 213/20* (2013.01); *H01M 4/38* (2013.01);
(Continued)

(58) Field of Classification Search
CPC .. H01M 12/085; H01M 4/38; H01M 10/4235; H01M 10/365; H01M 8/188;
(Continued)

(56) References Cited

U.S. PATENT DOCUMENTS

| 4,064,324 A | 12/1977 | Eustace |
| 4,065,601 A | 12/1977 | Ajami et al. |

(Continued)

FOREIGN PATENT DOCUMENTS

| GB | 2 005 064 | 4/1979 |
| WO | WO 2013/042103 | 3/2013 |

(Continued)

OTHER PUBLICATIONS

Co-pending U.S. Appl. No. 15/773,670, filed May 4, 2018.
(Continued)

*Primary Examiner* — Cynthia K Walls
(74) *Attorney, Agent, or Firm* — Nixon & Vanderhye P.C.

(57) ABSTRACT

The invention relates to a method of operating a zinc-bromine battery, especially at a high temperature, comprising adding 1-n-butyl-2-methyl-pyridinium bromide to the electrolyte of said battery, and charging or discharging said cell. Also provided is the use of 1-n-butyl-2-methyl-pyridinium bromide as an additive in a zinc-bromine battery operating at a temperature above 30° C., and an aqueous concentrate with high content of 1-n-butyl-2-methyl-pyridinium bromide.

2 Claims, 8 Drawing Sheets

(51) Int. Cl.
    *C07D 213/20* (2006.01)
    *H01M 8/18* (2006.01)
    *H01M 10/36* (2010.01)
    *H01M 10/42* (2006.01)
    *H01M 4/38* (2006.01)
    *H01M 4/02* (2006.01)

(52) U.S. Cl.
    CPC ......... *H01M 8/188* (2013.01); *H01M 10/365* (2013.01); *H01M 10/4235* (2013.01); *H01M 2004/027* (2013.01); *H01M 2300/0002* (2013.01); *Y02E 60/128* (2013.01)

(58) Field of Classification Search
    CPC .... H01M 2004/027; H01M 2300/0002; C07D 213/20; Y02E 60/128
    See application file for complete search history.

(56) References Cited

U.S. PATENT DOCUMENTS

| | | |
|---|---|---|
| 4,109,065 A | 8/1978 | Will et al. |
| 4,147,840 A | 4/1979 | Walsh et al. |
| 4,510,218 A | 4/1985 | Ando et al. |
| 4,631,240 A | 12/1986 | Walsh |

FOREIGN PATENT DOCUMENTS

| | | |
|---|---|---|
| WO | WO 2013/042110 | 3/2013 |
| WO | WO 2013/168145 | 11/2013 |
| WO | WO 2014/122641 | 8/2014 |

OTHER PUBLICATIONS

Cathro et al., "Selection of Quaternary Ammonium Bromides for Use in Zinc/Bromine Cells" *Journal of Power Sources*, 18 (1986) 349-370.
International Search Report issued in PCT/IL2016/051203 dated Jan. 30, 2017.
Written Opinion of the International Searching Authority issued in PCT/IL2016/051203 dated Jan. 30, 2017.
International Search Report for PCT/IL2016/050490, dated Aug. 17, 2016, 4 pages.
Written Opinion of the ISA for PCT/IL2016/050490, dated Aug. 17, 2016, 5 pages.

ADDITIVE FOR A FLOW BATTERY

This application is the U.S. national phase of International Application No. PCT/IL2016/050490 filed 9 May 2016, which designated the U.S. and claims the benefit of U. S. Provisional Application Nos. 62/159,395 filed 11 May 2015, and 62/253,148 filed 10 Nov. 2015, the entire contents of each of which are hereby incorporated by reference.

The invention relates to an additive for zinc-bromine flow batteries. The additive serves as a complexing agent, forming a complex with elemental bromine generated and utilized in zinc-bromine batteries.

In its simplest configuration, a zinc-bromine cell contains two chemically non-reactive electrodes and a separator located between the electrodes (e.g., an ion exchange membrane or microporous plastic sheet). The electrolyte used in the cell is an aqueous solution of zinc bromide, which is generally fed to the two compartments of the cell from two separate external reservoirs, utilizing a suitable circulation system. The term "anode" is used herein to indicate the electrode where metal zinc is formed (during charge) and oxidized (during discharge). The term "cathode" is used herein to indicate the electrode where elemental bromine is generated (during charge) and reduced (during discharge). The charge and discharge states of zinc-bromine battery will now be described in more detail.

During charge, an electric current is supplied to the cell from an external source, causing the deposition of zinc metal onto the anode and the concurrent generation of elemental bromine at the cathode, as shown by the following reaction:

$$Zn^{2+}{}_{(aq)}+2Br^{-}{}_{(aq)}\rightarrow Zn^{0}+Br_{2}$$

The aqueous electrolyte solution which circulates through the cathodic side during the cell charge contains a complexing agent, which is capable of forming a water-immiscible liquid phase upon complexing with elemental bromine. Thus, the elemental bromine generated at the cathodic side during cell charge reacts almost instantaneously with the water-soluble complexing agent, to form a water immiscible oily phase. The dense bromine-containing oily phase tends to settle at the bottom of the reservoir used for holding the catholyte. In this way, bromine is produced and stored in a reservoir outside the electrode.

During discharge, the reverse chemical reaction takes place and an electric current is drawn from the cell. The bromine-containing liquid, which forms part of the catholyte, is brought to the cathodic side of the cell, while the anolyte is simultaneously circulated through the anodic side. This results in the dissolution of the zinc anode to give zinc ions and the reduction of elemental bromine to form bromide ions (and the generation of electric current). The chemical reaction is represented by the following equation:

$$Zn^{0}+Br_{2}\rightarrow Zn^{2+}{}_{(aq)}+2Br^{-}{}_{(aq)}$$

Figure 1:
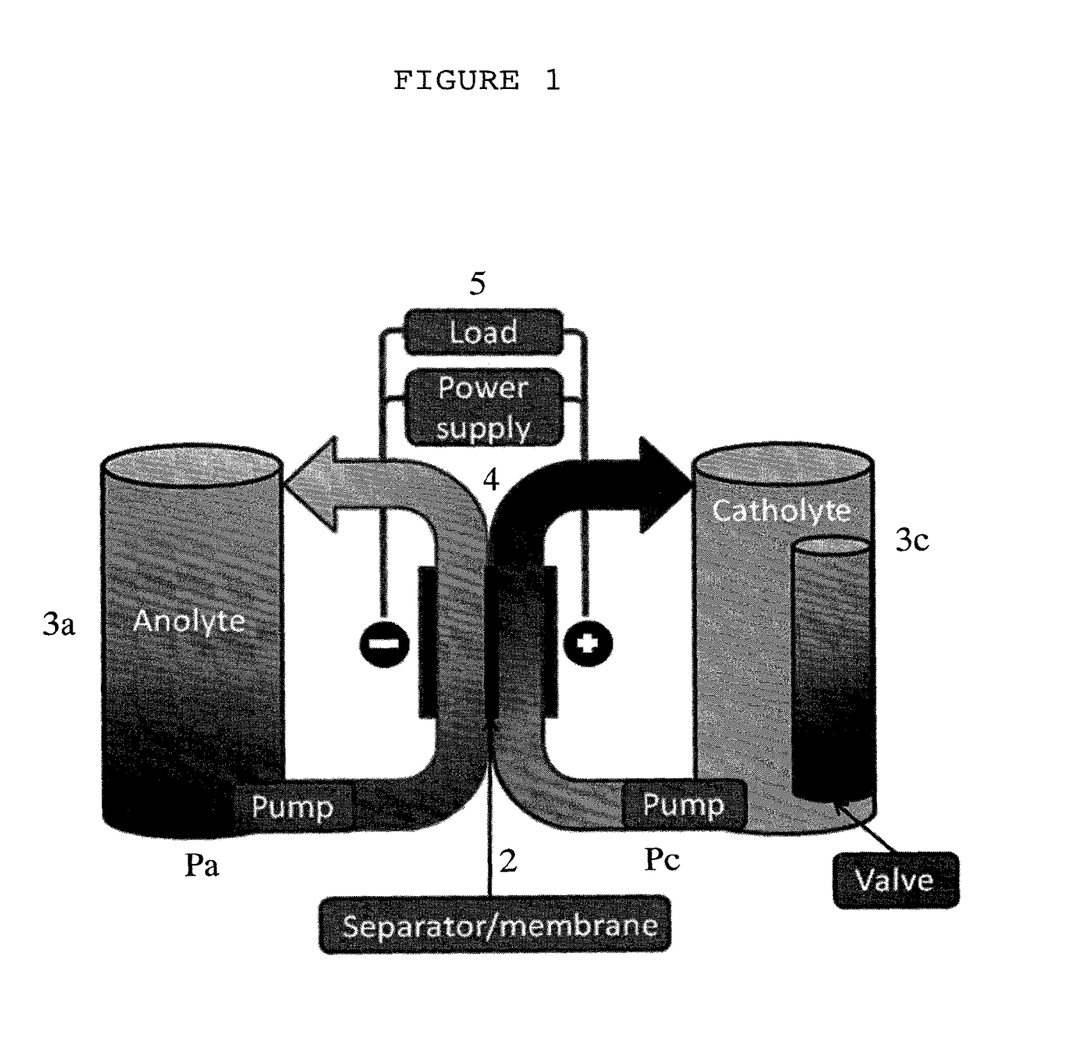
FIG. 1 is a schematic description of zinc-bromine cell.

FIG. 1 provides a schematic illustration of an example of a typical, separator-containing zinc-bromine cell, wherein numerals 1a and 1c indicate the anode and cathode, respectively, and numeral 2 represents the separator positioned between the electrodes. A reservoir for accommodating an aqueous solution of zinc bromide, used as the anolyte, is indicated by numeral 3a. Similarly, a reservoir 3c contains the catholyte, which consists of two liquid phases: an upper, aqueous solution of zinc bromide and a lower, dense organic phase comprising the elemental bromine in a form of a complex. The flow paths allowing the circulation of the anolyte and catholyte are respectively indicated by arrows (the streams are driven by pumps Pa, Pc). A suitable valve (v) allows injection of bromine into the flow path of the catholyte on discharge only. A power source and a load are electrically connected to the electrodes (numerals 4 and 5, respectively).

The simple cell configuration illustrated in FIG. 1 consists of two monopolar electrodes; commercial versions of zinc-bromine batteries are provided in a bipolar configuration, i.e., in the form of a stack consisting of bipolar electrodes placed in series between a pair of monopolar terminal electrodes.

Another configuration of zinc-bromine batteries is based on a membraneless electrochemical cell, devoid of a physical barrier (i.e., a separator) in the reaction zone between the electrodes. By removing the separator, several advantages can be gained. First, the internal resistance for the movement of ions from one compartment to the other, developed due to the presence of a physical barrier, is eliminated. Second, in a membraneless electrochemical cell, one electrolyte storage tank and one pump for circulating said electrolyte are used, which is certainly cost effective in comparison with the operation of the common zinc-bromine flow cell illustrated in FIG. 1, where two electrolyte tanks and two pumps are necessary.

As explained above, bromine-complexing agent (BCA) is added to the electrolyte of a zinc-bromine battery to minimize the vapor pressure of elemental bromine. Properties considered important for screening potential bromine-complexing agents include stability against crystallization down to low ambient temperatures (as low as 0° C. and even −5° C.), high conductivity of the electrolyte solution, low viscosity of the complex-containing oily phase and the ability to maintain a minimal, yet effective, amount of 'free bromine' in the aqueous phase.

Since zinc-bromine cell is alternately charged and discharged, its state of charge (SOC) varies continuously in a cyclic manner from 0% SOC (when the cell is completely discharged), theoretically up to 100% SOC (when the cell is fully charged; in practice, zinc-bromine batteries are charged up to ~50-70% SOC), and then on discharge back again to 0% SOC. In order to gain commercial acceptance, a bromine-complexing agent intended for use in zinc-bromine batteries needs to function satisfactorily at least across the interval ranging from 0% SOC to 50%-70% SOC.

As mentioned above, one of the chief requirements placed on a complexing agent is that it allows the presence of a minimal yet effective amount of 'free bromine' over the entire working SOC scale (by 'free bromine' is meant elemental bromine dissolved in the aqueous phase, as opposed to the bromine captured in the complex-containing oily phase). The presence of 'free bromine' is required at the lowermost range of the SOC scale (0%-~20% SOC), both in the cell charge and discharge stages. Before cell charging, a small amount of $Br_2$ in the electrolyte is useful to decrease overpotential. As to battery discharge, it must be borne in mind that if the availability of elemental bromine in the aqueous phase towards the end of the discharge process drops too sharply, i.e., on moving from 20 to 0% SOC, then a complete discharge state may not be reached.

In a series of recently published international publications (WO 2013/042110, WO 2013/168145 and WO 2014/122641) we reported the synthesis and properties of 1-alkyl-2-alkyl pyridinium bromide salts and 1-alkyl-3-alkyl pyridinium bromide salts. Specifically, the preparation of 1-ethyl-2-methyl pyridinium bromide (abbreviated 2-MEPy) and its use in hydrogen/bromine cells and zinc-bromine membraneless cells is demonstrated in WO 2013/042110 and WO 2013/168145, respectively. 1-alkyl-3-alkyl pyridinium bromide salts, especially 1-n-butyl-3-methyl pyridinium bromide (abbreviated 3-MBPy), have been shown to be effective bromine-complexing agents in zinc/bromine flow batteries (WO 2014/122641).

We have now found that 1-butyl-2-methyl pyridinium bromide, especially 1-n-butyl-2-methyl pyridinium bromide (abbreviated herein 2-MBPy) demonstrates very good bromine-complexing activity in zinc bromine flow batteries over the entire SOC scale. In particular, the experimental results reported below indicate that 2-MBPy displays better properties in comparison with the structurally similar complexants 3-MBPy and 2-MEPy, over the low range of the SOC scale. 2-MBPy provides an acceptable concentration of 'free bromine' from the very beginning of the charge reaction. The viscosity of the oily phase consisting of a complex of 2-MBPy with bromine molecules is lower than the viscosity of the corresponding complexes formed with 3-MBPy. Another effect observed on oxidizing bromide to $Br_2$ in aqueous zinc bromide in the presence of either 2-MBPy, 3-MBPy or 2-MEPy (when the compositions of the tested solutions correspond to some discrete points in the low range of the SOC scale) is that electrode voltage remains essentially constant in the 2-MBPy-containing solutions, with magnitude lesser than the magnitude of electrode voltage measured on oxidizing bromide in the presence of 3-MBPy or 2-MEPy.

Accordingly, one aspect of the invention relates to an electrolyte solution suitable for use in a zinc-bromine battery, comprising zinc bromide and a liquid complex composed of 1-butyl-2-methyl-pyridinium bromide, especially 1-n-butyl-2-methyl pyridinium bromide, combined with one or more bromine molecules.

Another aspect of the invention is the use of 1-butyl-2-methyl pyridinium bromide, especially 1-n-butyl-2-methyl pyridinium bromide, as an additive in the electrolyte solution of zinc bromine flow cells.

In yet another aspect, the invention is directed to a method of operating a zinc-bromine battery, comprising adding 1-butyl-2-methyl pyridinium bromide, especially 1-n-butyl-2-methyl-pyridinium bromide, to the electrolyte of said battery, and charging or discharging said cell.

1-n-butyl-2-methyl-pyridinium bromide is prepared by the reaction of 2-picoline with 1-bromobutane (n-butyl bromide) as shown below:

The reaction of 2-picoline with 1-bromobutane (both are liquids at room temperature) may take place either in a solvent-free reaction medium, in the presence of water or in an organic solvent such as acetonitrile, ethyl acetate or toluene. The reactants are either used in equimolar amounts, or one of the reactants (1-bromobutane or 2-picoline) could be applied in an excess of up to 30 molar %. In view of the utility of 1-n-butyl-2-methyl-pyridinium bromide as an additive for an electrolyte solution utilized in zinc-bromine flow batteries, it is convenient to collect the product in the form of a concentrated aqueous solution which could be directly added into, and easily mixed with, the aforementioned electrolyte solution. Thus, the processes described below are preferably designed to produce an aqueous concentrate of 1-n-butyl-2-methyl-pyridinium bromide in a direct manner; these processes are devoid of the formation, isolation and purification of the compound in a solid state.

In one embodiment, the reaction of 2-picoline with 1-bromobutane takes place in a solvent-free medium under pressure. The progressively formed 1-n-butyl-2-methyl-pyridinium bromide is kept in a liquid state throughout the reaction and workup stages and the liquid product is combined with water to form the aqueous concentrate. To this end, a pressure reactor is charged with 2-picoline and heated to a temperature of not less than 70° C. The 1-bromobutane is then fed slowly to the reaction vessel, e.g., via drop-wise addition. The reaction is exothermic; the temperature in the reaction mixture increases above 120° C. during the gradual feeding of the reactant. The reaction mixture is then further maintained at about 80 to 110° C. for not less than 60 minutes, whereby the reaction goes to completion. Following addition of deionized water to the pressure reactor and release of pressure, the liquid reaction mass is discharged from the reactor and is subjected to one more purification cycles consisting of water addition and evaporation. Ultimately the amount of water is adjusted to afford a concentrate aqueous composition with very high content of 1-n-butyl-2-methyl-pyridinium bromide (>75% by weight, preferably >80% by weight).

The reaction of 2-picoline with 1-bromobutane is also manageable under atmospheric pressure in the presence of water. In this case, the gradual addition of 1-bromobutane to a reaction vessel which has been previously charged with 2-picoline is carried out at a temperature in the range from 80 to 110° C. for not less than 1 hour, with water being added from time to time (the volumetric ratio 1-bromobutane:water may be from 3:1 to 18:1). On completion of the addition of 1-bromobutane, the reaction mixture is kept under heating for not less than 1 hour, at a temperature of not less than 70° C. The reaction product is then combined with deionized water and undergoes repeated distillation as described above. Ultimately the product is recovered in the form of a concentrated aqueous solution.

Alternatively, the reaction of 2-picoline with 1-bromobutane is carried out in an organic solvent such as acetonitrile. A reaction vessel is charged with the solvent and 2-picoline, heated to reflux, followed by the slow addition of 1-bromobutane. On completion of the addition of 1-bromobutane, the reaction mixture is allowed to stand under heating at a temperature of not less than 70° C. for at least 1 hour to reach completion. The reaction mixture is cooled down, the organic solvent is removed by evaporation and water is added. Typically the reaction mass is subjected to further evaporation before the amount of water is eventually adjusted to obtain 1-n-butyl-2-methyl-pyridinium bromide in the form of a concentrated aqueous solution (e.g., having concentration of more than 80% by weight). A concentrate aqueous composition with very high content of 1-n-butyl-2-methyl-pyridinium bromide (>75% by weight, preferably >80% by weight, e.g., from 75 to 85% by weight 2-MBPy content) forms another aspect of the invention.

1-n-butyl-2-methyl-pyridinium bromide can be added to the zinc bromide solution in any suitable form, e.g., as a solid or as a clear aqueous solution prepared as set forth above, which solution can be conveniently injected into the electrolyte circulating in an energy storage device based on zinc/bromine flow cells. A suitable aqueous electrolyte solution which may be used in zinc bromine batteries has the following composition: $ZnBr_2$ at a concentration from 0.5M to 5.0 M, (preferably 1.0 to 3.0 M, e.g., from 2.0 to 3.0 M); a complexing agent at a concentration of not less than 0.25M, e.g., from 0.25M-2.5M, and optionally, one or more water soluble salts such as halide salts, e.g., zinc chloride, sodium chloride or potassium chloride, and also sulfate salts (these salts serve as conductivity enhancers). The total concentration of the secondary water-soluble salts, which may optionally be present in the electrolyte solution, can be up to 3.5 M, e.g., between 0.5-3.5 M. It is noted that the electrolyte may further contain added bromine or in-situ chemically generated bromine, as described in WO 2013/042103, and also the electrochemically generated bromine (which is formed in-situ in the cell on charging). On charging, the zinc bromide is consumed and bromine is generated. On discharging, the aqueous phase of the electrolyte is again concentrated with respect to $ZnBr_2$, and the concentration of elemental bromine is decreased.

It should be noted that an upper limit to the free bromine concentration range arises from the requirement to minimize the occurrence of the non-faradaic reactions in the negative side of the cell (unfortunately, no separator can totally prevent bromine migration to the anode side; in the membraneless cell configuration, the requirement placed on the amount of 'free bromine' is even more stringent). The complexation ability of complexing agents towards elemental bromine generally decreases with increasing temperature, meaning that the concentration of the 'free bromine' in the aqueous electrolyte increases with increasing temperature. Surprisingly, the additive according to the invention exhibits strong complexation ability also at elevated temperatures, as indicated by the experimental results reported below, showing that the additive is very efficient in keeping the aqueous phase bromine concentration low at high temperatures. In the presence of 2-MBPy, the free bromine concentration varies only slightly with increasing temperature, namely, 2-MBPy is able to maintain an essentially constant low free bromine concentration over a broad range of elevated working temperatures, and across the progressively varying states of charge.

Accordingly, the invention is directed to a method of operating a zinc-bromine battery, comprising adding 1-butyl-2-methyl pyridinium bromide, especially 1-n-butyl-2-methyl-pyridinium bromide, to the electrolyte of said battery, and charging or discharging said cell, wherein the battery operates at a temperature above 30° C., e.g., above 35° C. and above 40° C. (for example, from 35° C. to 60° C., e.g., from 40 to 55° C.). Structures of zinc/bromine batteries which can employ the electrolyte of the invention are known in the art and are described, e.g., in U.S. Pat. Nos. 4,109,065, 4,510,218 and WO 2013/042103.

EXAMPLES

Examples 1 (of the Invention) and 2-3 (Comparative)

Properties of Zinc Bromide Electrolyte Solutions with Different Complexing Agents To test the utility of 2-MBPy, 3-MBPy and 2-MEPy as bromine-complexing agents in zinc-bromine batteries, 100 ml samples of zinc bromide electrolyte solutions were prepared, with varying amounts of zinc bromide and elemental bromine as tabulated in Table 1, to match different states of charge. Each sample contains, in addition to the aqueous solution of zinc bromide and elemental bromine, also zinc chloride at a concentration of 0.4M-0.5M. The samples were stored at 25° C. or 35° C. for 24-48 hours after preparation before any measurement was conducted. The samples which were tested at 25° C. contain also potassium chloride at a concentration of 1.0M.

The following properties of interest were measured:

(i) Bromine concentration in the aqueous phase above the polybromide complex-oily phase was determined by a conventional iodometric titration technique. Each vial was sampled two times (measurements were carried out at 25° c. and 35° C.)

(ii) Viscosity of the complex containing-oily phase was measured at 35° C., using Cannon-Fenske Opaque Viscometer.

(iii) Constant-current electrolysis experiments were run and electrode voltage was measured on oxidizing bromide to elemental bromine at 35° C. The experimental set-up consists of a glassy carbon rotating-disc electrode (having diameter of 3 mm and area of 0.07 $cm^2$), which was set up to rotate at 2400 rpm; a counter electrode (a titanium electrode having much larger active area, of about 5 $cm^2$) and a standard calomel electrode as a reference electrode.

The foregoing properties were measured for each of the additives under consideration at different compositions of the electrolyte solution, matching different states of charge (the 0% to 100% SOC scale was investigated at 20% increments, i.e., at six discrete points). The results are set out in Table 1.

TABLE 1

| Ex. | % SOC | $ZnBr_2$ M | $Br_2$ M | Additive M | [aq. $Br_2$] M (25° C.) | [aq. $Br_2$] M (35° C.) | Viscosity cP (35° C.) | Voltage V (35° C.) |
|---|---|---|---|---|---|---|---|---|
| 1A | 0 | 1.6 | 0.16 | 2- | 0.0039 | 0.004 | 50 | 1.064 |
| 1B | 20 | 1.28 | 0.33 | MBPy | 0.0043 | 0.004 | 55 | 1.069 |
| 1C | 40 | 0.96 | 0.65 | 0.8M | 0.0044 | 0.005 | 48 | 1.070 |
| 1D | 60 | 0.64 | 0.99 | | 0.0080 | 0.007 | ND | ND |

TABLE 1-continued

| Ex. | % SOC | ZnBr$_2$ M | Br$_2$, M | Additive M | [aq. Br$_2$] M (25° C.) | [aq. Br$_2$] M (35° C.) | Viscosity cP (35° C.) | Voltage V (35° C.) |
|---|---|---|---|---|---|---|---|---|
| 1E | 80 | 0.32 | 1.35 | | 0.0116 | 0.015 | ND | ND |
| 1F | 100 | 0.08 | 1.7 | | 0.0123 | 0.017 | ND | ND |
| 2A | 0 | 1.6 | 0.16 | 3- | 0.0001 | 0.001 | 65-70 | 1.079 |
| 2B | 20 | 1.28 | 0.33 | MBPy | 0.0019 | 0.004 | 65 | 1.081 |
| 2C | 40 | 0.96 | 0.65 | 0.8M | 0.0034 | 0.006 | 60 | 1.098 |
| 2D | 60 | 0.64 | 0.99 | | 0.0049 | 0.007 | ND | ND |
| 2E | 80 | 0.32 | 1.35 | | 0.0107 | 0.013 | ND | ND |
| 2F | 100 | 0.08 | 1.7 | | 0.0123 | 0.016 | ND | ND |
| 3A | 0 | 1.6 | 0.16 | 2- | ND | 0.030 | ND | ND |
| 3B | 20 | 1.28 | 0.33 | MEPy | ND | 0.020 | ND | ND |
| 3C | 40 | 0.96 | 0.65 | 0.8M | ND | 0.018 | ND | ND |
| 3D | 60 | 0.64 | 0.99 | | ND | 0.019 | ND | ND |
| 3E | 80 | 0.32 | 1.35 | | ND | 0.020 | ND | ND |
| 3F | 100 | 0.08 | 1.7 | | ND | 0.018 | ND | ND |

Figure 2:
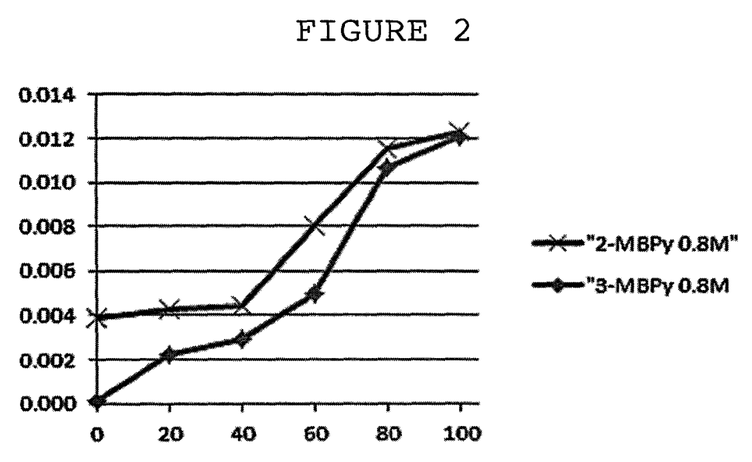
FIG. 2 is a graph where the concentration of elemental bromine in the aqueous phase is plotted against SOC at 25° C. for 2-MBPy and 3-MBPy.
Figure 3A:
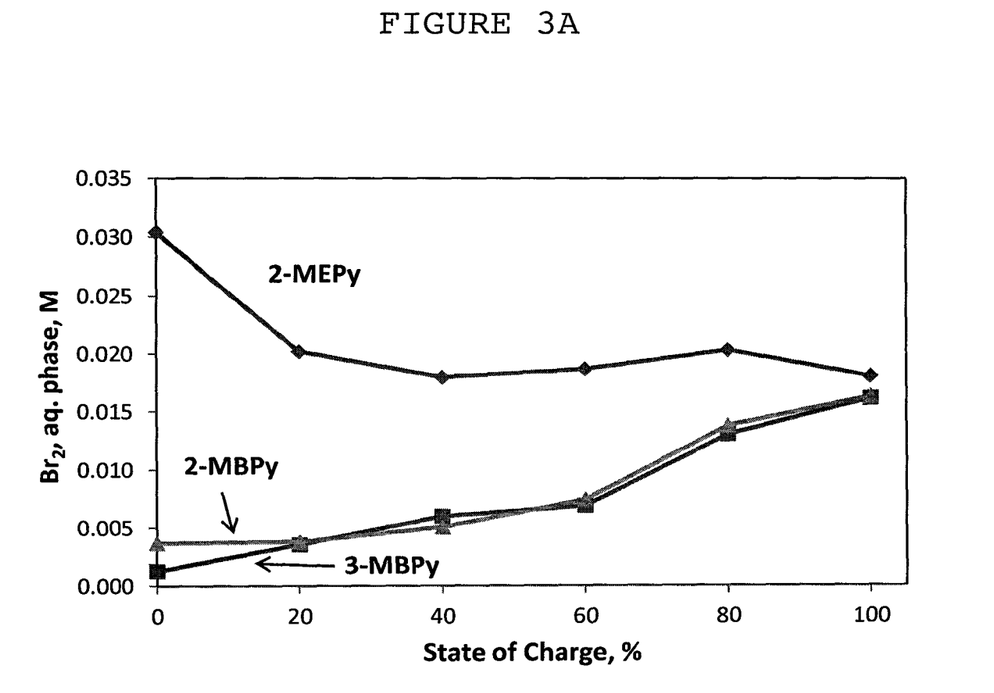
FIG. 3A is a graph where the concentration of elemental bromine in the aqueous phase is plotted against SOC at 35° C. for 2-MBPy, 3-MBPy and 2-MEPy.
Figure 3B:
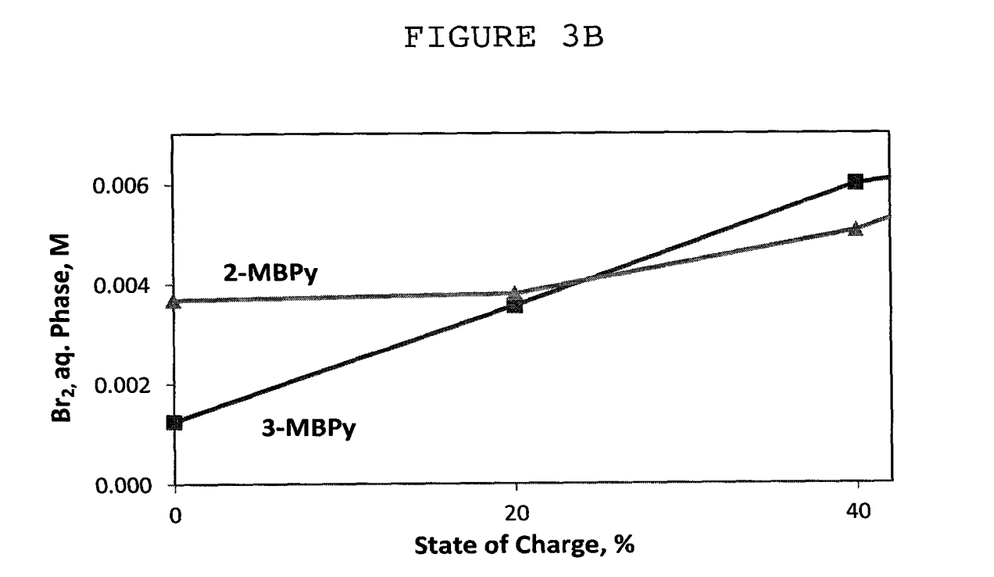
FIG. 3B is a graph where the concentration of elemental bromine in the aqueous phase is plotted against SOC (the 0-40% interval only) at 35° C. for 2-MBPy and 3-MBPy.

In FIGS. 2, 3A and 3B, the concentration of elemental bromine in the aqueous phase is plotted against the SOC (measured at 25° C.—FIG. 2; and 35° C.—FIGS. 3A and 3B). The curves shown in the Figures illustrate the ability of 2-MBPy to maintain a workable concentration of aqueous bromine from the very beginning of the charge process, all the way round to the fully charged state.

Regarding 3-MBPy, the advantage of 2-MBPy over 3-MBPy is observed at the low state of charge both at 25° C. and 35° C., in the range from 0% to 20% SOC (FIG. 3B provides an enlarged representation of the interval of interest). The increased concentration of bromine in the aqueous phase of the electrolyte solution, together with consistently lower viscosity and lower charge voltage measured across the 0% SOC to 40% SOC interval for the 2-MBPy-containing samples vis-à-vis the 3-MBPy containing samples, indicate that 2-MBPy is suitable for use as bromine-complexing agent in zinc-bromine batteries.

As to 2-MEPy, the concentration of elemental bromine in the aqueous phase of the electrolyte solution when 2-MEPy is the added BCA is too high for membraneless cell configuration. This high concentration would lead to self-discharge and decreased current efficiency, namely, the efficiency of zinc plating formed onto the anode surface, when the cell is charged at a fixed current density, would be unsatisfactory.

Examples 4 to 6 (Comparative) and 7 (of the Invention)

Figure 4:
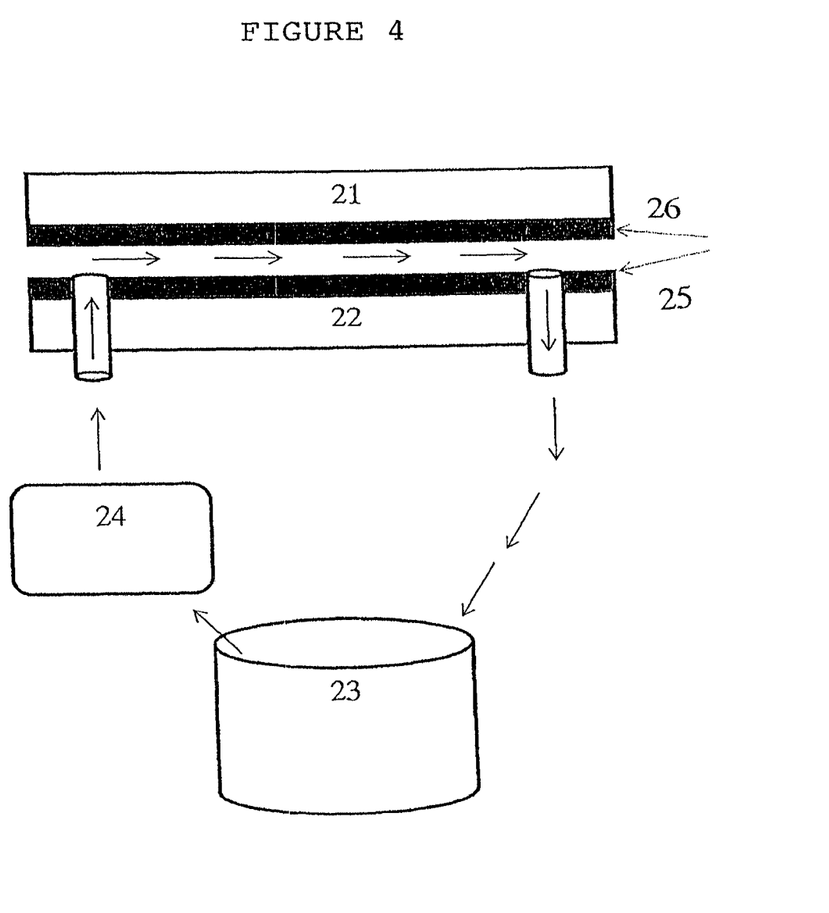
FIGS. 4 and 5 illustrate an experimental set-up used.

Testing Zinc Bromide Electrolyte Solutions with Different Bromine-Complexing Agents (BCA) in an Electrochemical Experimental Set-Up An experimental set-up schematically illustrated in FIG. 4 was used to evaluate the effect of the presence of various bromine complexing agents on the efficiency of the operation of zinc/bromine membraneless cell. A characteristic property of the cell which was chosen for the quantitative study is the efficiency of zinc plating formed onto the anode surface, when the cell is charged at current density of 60 mA/cm$^2$.

During charge, zinc metal is increasingly formed on the anode and elemental bromine is increasingly generated in the electrolyte. In the set of experiments described below, various bromine-complexing agents were added to zinc bromide aqueous electrolyte which was recirculated in a membraneless electrochemical cell configuration during charge, and the bromine-complexing agents were tested for their ability to capture and hold the elemental bromine in the form of water-immiscible phase, minimizing the dissolution of elemental bromine in the aqueous phase of the electrolyte and correspondingly lessening the direct chemical oxidation of the zinc by the elemental bromine present in the aqueous phase. Thus, in membraneless cells, in the absence of physical membrane separating between the zinc and bromine electrodes, the plating efficiency of the zinc critically depends on the efficacy of the bromine-complexing agent.

The Experimental Set-Up

Figure 5:
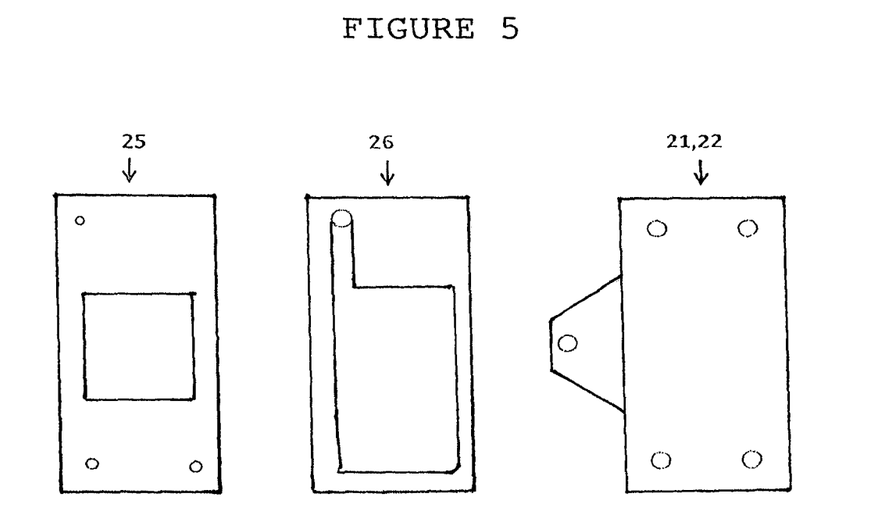

Referring to FIG. 4, the experimental set-up comprises a pair of graphite electrodes 21 and 22 which serve as zinc and bromine electrodes, respectively. The electrode plates are made of compressed graphite particles, are rectangular in shape and are about 5 mm thick, with a trapezoidal section laterally extending from one of the long sides of the rectangular electrodes, as shown in FIG. 5, which provides a top view of the electrodes. Electrodes 21 and 22 are mounted horizontally, in parallel to one another, and are spaced 2 mm apart, with zinc electrode 21 being positioned on top of bromine electrode 22.

Within the space between the two electrodes, 1 mm thick Viton® gasket frame 25 is placed over the upper face of bromine electrode 22, and 1 mm thick Viton® flow frame 26 is disposed on top of gasket 25. A top view of elements 25 and 26 is presented in FIG. 5, showing the open central regions thereof (note that the open regions are not equal, and are not in scale). Therefore, the lower and upper faces of electrodes 21 and 22, respectively, are covered, except for a central region which is left exposed on each of said electrodes faces. The non-coated central regions of the electrodes are hence available for the electrochemical reactions. The electrochemically-reactive central regions on the lower and upper faces of electrodes 21 and 22, respectively, coincide with one another with respect to position, geometric shape and size. Each of the two opposed electrochemically-reactive central regions has an area of 10 cm$^2$. It is noted that no membrane is interposed in the space between the electrodes.

The electrode plates are perforated to allow the access and exit of electrolyte flow.

The Compositions of the Tested Solutions 100 ml samples of aqueous electrolyte solutions were prepared, with the following compositions:
[ZnBr$_2$]=2.0 M, [Br$_2$]=0.25 wt %, [BCA]=0.8M and [ZnCl$_2$]=0.4 M A typical composition of an electrolyte solution at the beginning of the charging process, i.e., an electrolyte solution corresponding to 0% SOC, has the concentrations set forth above (note that a small amount of elemental bromine is normally added to avoid overpotential).

During the experiments, while the electrolysis is in progress, the composition of the solutions gradually varies, with the concentrations of zinc bromide and elemental bromine decreasing and increasing, respectively. In the present experiments, the electrolysis was allowed to proceed until the composition of the solution reached a state of charge of 40%. Thus, the activity of the bromine-complexing agents (BCA) was investigated across the to 40% SOC range. The BCA tested in Examples 4 to 7 were 3-MBPy, 2-MEPy, MEP (N-methyl-n-ethyl-pyrrolidinium bromide, a commonly used bromine-complexing agent) and the BCA of the invention, 2-MBPy, respectively.

The Experiments

All the experiments were carried out at temperature of 35° C., with the cell being charged at 0.6 A, i.e., current density of 60 mA/cm². Before use, the electrolyte solution was kept at 35° C. for at least twenty four hours.

Each experiment is run as follows. The electrolyte solution is held in a reservoir 23, where it is stirred with the aid of a magnetic stirrer at a rate of 150 rpm. The electrolyte volume is 100 ml (~110-130 g). Reservoir 23 is kept at a temperature of 36±0.1° C. Peristaltic pump 24, operating at a constant rate, drives the electrolyte solution through the cell, causing the solution to flow in the space between electrodes 21 and 22. The flow path of the electrolyte is schematically indicated by means of arrows in FIG. 4; note the single inlet opening and the pair of outlet openings, to prevent accumulation of the complex inside the cell. The electrolyte solution is drawn from the upper (aqueous) part of the electrolyte volume and returned to the bottom of reservoir 23, where the dense (organic) phase accumulates.

Each experiment lasted about 4.0-4.5 hours (or less, due to short circuit caused by dendrite growth inside the cell). At the end of the experiment, the cell was opened and photos of the two electrodes were taken immediately. The cell components were then washed in a soap solution and distilled water, and were allowed to dry. The weight of Zn deposit was determined. Plating efficiency was calculated as follows:

$$\text{Plating efficiency} = \frac{M}{\left(\frac{I*t}{F}\right)*\left(\frac{Mw}{z}\right)} *100$$

M—mass of zinc deposited on the electrode
I—electrical current (0.6 A)
t—time during which the current passed through the cell (sec)
F—Faraday constant (96485 C/mol)
Mw—molecular weight (g/mol)
z—metal valence (2)

The experimental details and the results are tabulated in Table 2.

TABLE 2

| Ex. | Time (h) | % SOC | ZnBr$_2$ (M) | BCA | [BCA] (M) | plating efficiency % |
|---|---|---|---|---|---|---|
| 4 | 4.0 | 0→40 | 2.0→1.2 | 3-MBPy | 0.8 | 80 |
| 5 | 4.5 | 0→20 | 2.0→1.6 | 2-MEPy | 0.8 | 25 |
| 6 | 4.5 | 0→15 | 2.0→1.8 | MEP | 0.8 | <20 |
| 7 | 4.0 | 0→40 | 2.0→1.2 | 2-MBPy | 0.8 | 89 |

The results indicate that 2-MBPy is an excellent bromine-complexing agent, achieving the highest plating efficiency during the electrolysis (cell charging).

Figure 6A:
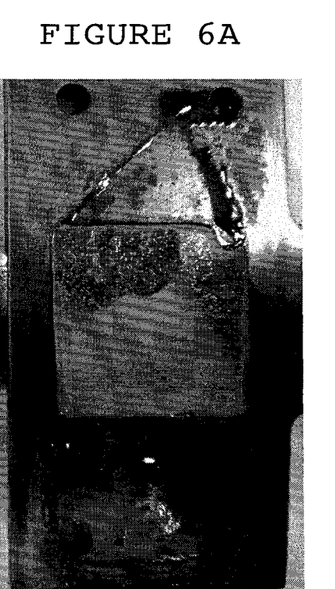
FIGS. 6A and 6B are photos of the bromine electrode and zinc electrode, respectively, taken immediately on completion of the an experiment with 3-MBPy.
Figure 6B:
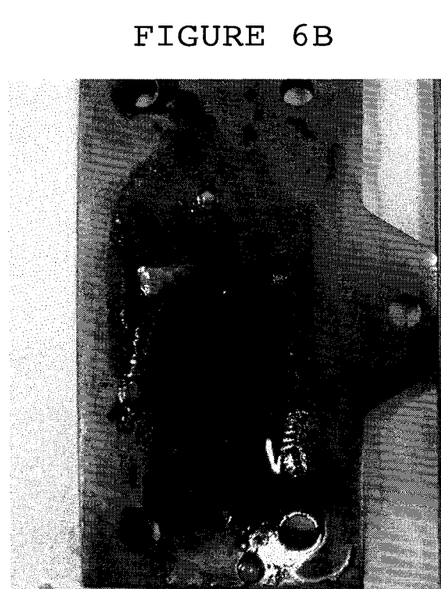

FIGS. 6A and 6B are photos of the bromine electrode and zinc electrode, respectively, taken immediately on completion of the experiment with 3-MBPy. It may be seen that a growth of zinc dendrites took place on the face of the zinc anode, in the region which corresponds in position to the region of the face of the parallel-opposed bromine cathode in which the complex accumulated.

Figure 7A:
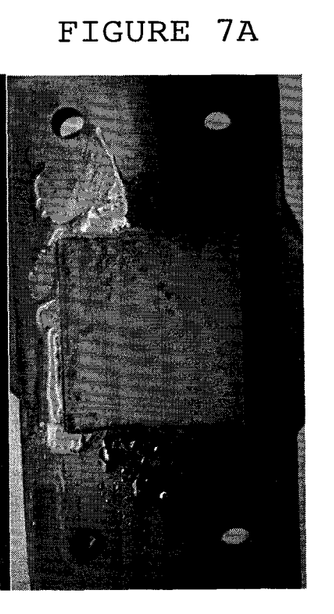
FIGS. 7A and 7B are photos of the bromine electrode and zinc electrode, respectively, taken immediately on completion of an experiment with 2-MBPy.
Figure 7B:
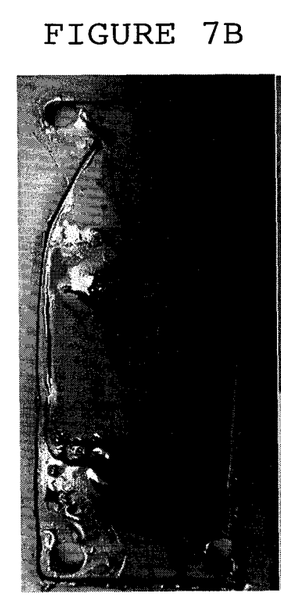

FIGS. 7A and 7B are photos of the bromine electrode and zinc electrode, respectively, taken immediately on completion of the experiment with 2-MBPy. It may be seen that the zinc plating deposited onto the anode surface is more uniform, with significantly lesser dendrites formation observed.

Examples 8 to 13

8, 10 and 12 of the Invention; 9, 11, 13 Comparative

Testing the Physic-Chemical Properties of Zinc Bromide Electrolyte Solutions with Different Bromine-Complexing Agents (BCA) at High Temperatures Range To test the utility of 2-MBPy and 3-MBPy as bromine-complexing agents at high operating temperature zinc-bromine batteries, 100 ml samples of zinc bromide electrolyte solutions were prepared, with varying amounts of zinc bromide and elemental bromine as tabulated in Table 3 below, to match different states of charge. Each sample contains, in addition to the aqueous solution of zinc bromide and elemental bromine, also zinc chloride at a concentration of 0.3M-0.5M. The samples were stored at 40° C., 50° C. or 55° C. for 24 hours after preparation before any measurement was conducted. All measurements and sampling were carried out at the storing temperatures.

The following properties of interest were measured:

(i) Bromine concentration in the aqueous phase above the polybromide complex-oily phase was determined by a conventional iodometric titration technique. Each vial was sampled two times (measurements were carried out at 40° C., 50° C. and 55° C.)

(ii) Viscosity of the complex containing-oily phase was measured at 40° C., 50° C. and 55° C., using Cannon-Fenske Opaque Viscometer.

(iii) Concentration of the BCA in the aqueous phase was measured with chromatographic techniques. Aqueous phase samples were taken at 40° C., 50° C. and 55° C.

(iv) Specific conductivity of the aqueous phase was measured using a bi-plate conductivity meter at 40° C., 50° C. and 55° C.

The foregoing properties were measured for each of the additives under consideration at different compositions of the electrolyte solution, matching different states of charge (the 0% to 100% SOC scale was investigated at the end-points and midpoint, i.e., at 0%, 50% and 100% SOC). The results are set out in Table 3.

TABLE 3

| Ex. | % SOC | ZnBr$_2$ M | Br$_2$ M | Additive M | [aq. Br$_2$] M (40° C.) | Viscosity cP (40° C.) | [aq. BCA] M (40° C.) | Specific Cond. mS/cm (40° C.) |
|---|---|---|---|---|---|---|---|---|
| 8A | 0 | 1.6 | 0.5 | 2-MBPy | 0.0062 | 42 | 0.1209 | 124 |
| 8B | 50 | 0.9 | 1.12 | 1M | 0.0085 | 26 | 0.0509 | 131 |
| 8C | 100 | 0.2 | 1.7 | | 0.0168 | 15 | 0.0081 | 114 |
| 9A | 0 | 1.6 | 0.5 | 3-MBPy | 0.0050 | 42 | 0.0810 | 129 |
| 9B | 50 | 0.9 | 1.12 | 1M | 0.0071 | 22 | 0.0424 | 132 |
| 9C | 100 | 0.2 | 1.7 | | 0.0162 | 14 | 0.0063 | 114 |

TABLE 3-continued

| Ex. | % SOC | ZnBr$_2$ M | Br$_2$, M | Additive M | [aq. Br$_2$] M (50° C.) | Viscosity cP (50° C.) | [aq. BCA] M (50° C.) | Specific Cond. mS/cm (50° C.) |
|---|---|---|---|---|---|---|---|---|
| 10A | 0 | 1.6 | 0.5 | 2-MBPy | 0.0071 | 24 | 0.1278 | 139 |
| 10B | 50 | 0.9 | 1.12 | 1M | 0.0092 | 18 | 0.0535 | 144 |
| 10C | 100 | 0.2 | 1.7 | | 0.0171 | 11 | 0.0083 | 125 |
| 11A | 0 | 1.6 | 0.5 | 3-MBPy | 0.0075 | 27 | 0.1042 | 142 |
| 11B | 50 | 0.9 | 1.12 | 1M | 0.0108 | 15 | 0.0469 | 144 |
| 11C | 100 | 0.2 | 1.7 | | 0.0203 | 10 | 0.0072 | 125 |

| Ex. | % SOC | ZnBr$_2$ M | Br$_2$, M | Additive M | [aq. Br$_2$] M (55° C.) | Viscosity cP (55° C.) | [aq. BCA] M (55° C.) | Specific Cond. mS/cm (55° C.) |
|---|---|---|---|---|---|---|---|---|
| 12A | 0 | 1.6 | 0.5 | 2-MBPy | 0.0072 | 20 | 0.1407 | 143 |
| 12B | 50 | 0.9 | 1.12 | 1M | 0.0095 | 15 | 0.0582 | 149 |
| 12C | 100 | 0.2 | 1.7 | | 0.0181 | 11 | 0.0094 | 129 |
| 13A | 0 | 1.6 | 0.5 | 3-MBPy | 0.0081 | 21 | 0.1304 | 150 |
| 13B | 50 | 0.9 | 1.12 | 1M | 0.0114 | 13 | 0.0546 | 151 |
| 13C | 100 | 0.2 | 1.7 | | 0.0225 | 9 | 0.0081 | 129 |

The results set forth in Table 3 indicate that electrolyte solutions, which contain either 2-MBPy or 3-MBPy, display comparable conductivities and viscosities. However, the complexation abilities of 2-MBPy and 3-MBPy show different dependence on temperature. In the case of 2-MBPy, the concentration of aqueous bromine increases only slightly with increasing temperature. 3-MBPy, on the other hand, shows stronger temperature dependence, seeing that the concentration of the aqueous bromine increases more sharply in the temperature range under consideration. Thus, 2-MBPy is more effective in keeping the aqueous phase bromine concentration low at high temperatures.

To better appreciate these findings, the experimental results are also presented graphically.

Figure 8A:
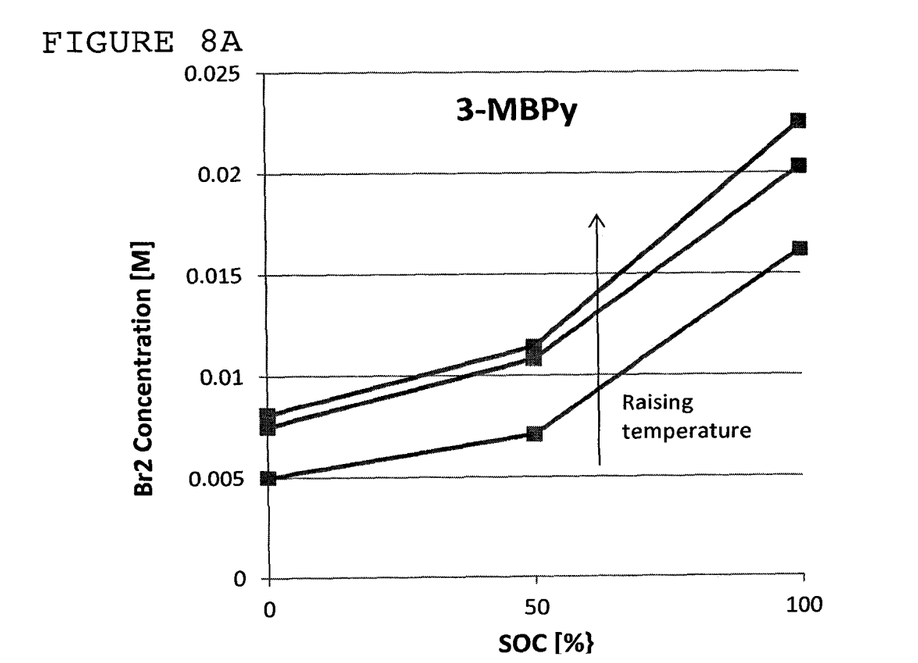
FIGS. 8A and 8B are graphs where the concentration of aqueous bromine is plotted against SOC for 3-MBPy and 2-MBPY-containing electrolyte solutions, respectively, at three different temperatures.
Figure 8B:
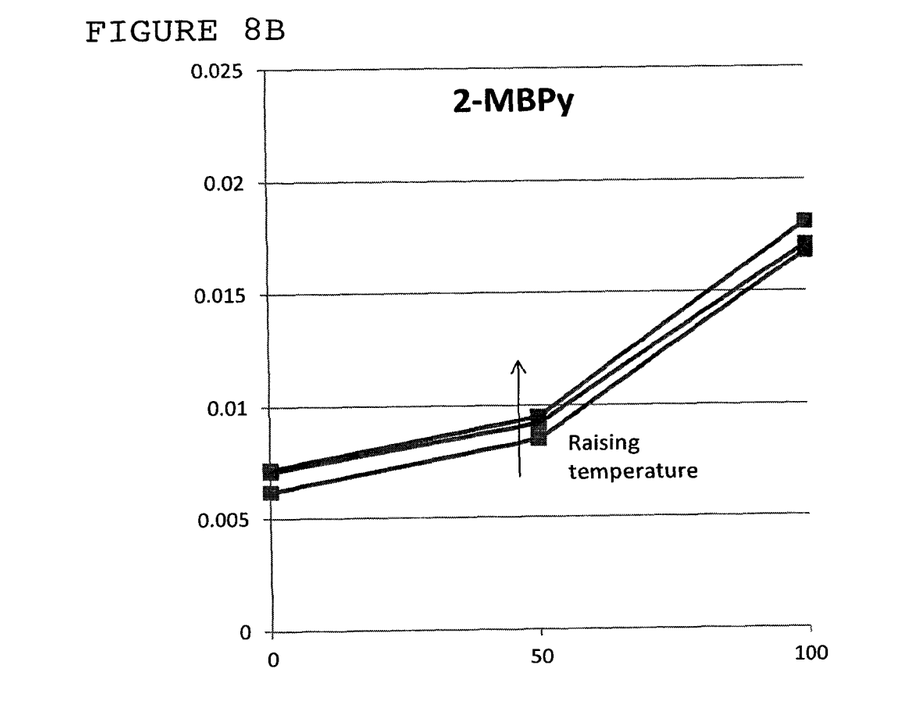

In the graphs shown in FIGS. 8A and 8B, the concentration of aqueous bromine is plotted against the state of charge for the 3-MBPy and 2-MBPY-containing electrolyte solutions, respectively. In each graph, three separate curves are plotted, which correspond to measurements conducted at 40° C., 50° C. and 55° C. (the curves are not labeled; an upward pointing arrow in the graph indicates the 40° C.→50° C.→55° C. temperature increase). It is seen that in the case of 2-MBPy, the three individual curves are only very slightly separated from each other.

Figure 9A:
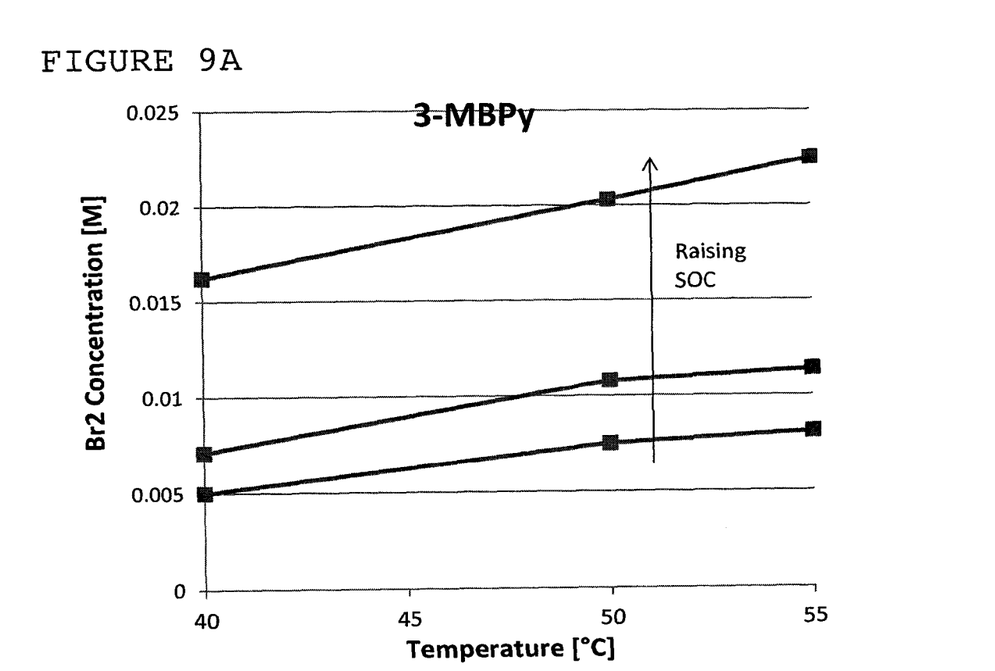
FIGS. 9A and 9B are graphs where the aqueous bromine concentration is plotted against temperature, for 3-MBPy and 2-MBPY-containing electrolyte solutions, respectively, at three different SOC.
Figure 9B:
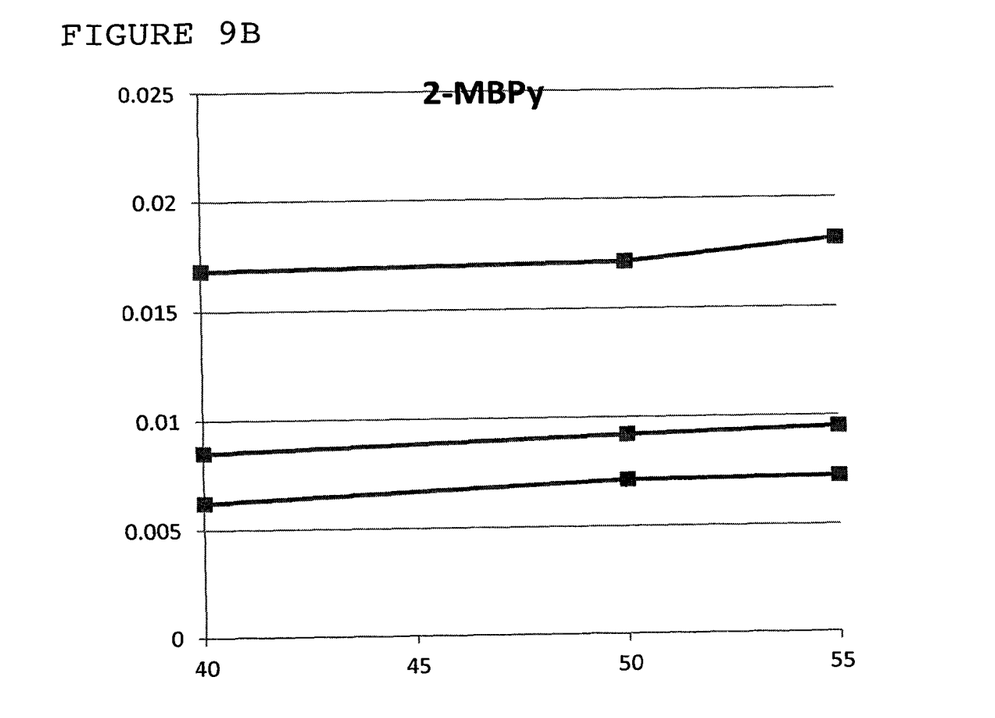

The same experimental results are also shown in the graphs of FIGS. 9A and 9B, where the aqueous bromine concentration is plotted against temperature, for the 3-MBPy and 2-MBPY-containing electrolyte solutions, respectively. In each graph three distinct concentration vs. temperature curves are shown, corresponding to the three distinct state of charge investigated (0%, 50% and 100%; the individual curves are not labeled; an upward pointing arrow in the graph indicates the 0%→50%→100% change in the state of charge). In the case of 2-MBPy, the weak temperature dependence of the aqueous bromine concentration is clearly evident in each of the states of charge investigated; steeper slopes are observed for the curves produced for 3-MBPy.

Preparation 1

Preparation of 1-n-butyl-2-methyl pyridinium bromide (2-MBPy)

A double surface pressure reactor was equipped with a mechanical stirrer, a thermocouple well and a dosing pump. The reactor was charged with 2-picoline (250 g) and heated to 100-104° C. n-butyl bromide (358.8 g) was then continuously fed during 3 hours. During feeding the temperature rose up to 124-129° C. Maximal pressure during feeding stage was 1.5 barg. After feeding was completed the reaction mixture was heated for 2 hours (110-105° C.). DIW (100 mL) was added, the pressure was released and the mixture removed from the reactor through the bottom valve. The mixture was evaporated using a rotavapor. Additional DIW (100 g) was added and the mixture was re-evaporated. DIW was added for dilution. Final product: 685 g, 82 weight % (argentometric titration); 93% yield.

Preparation 2

Preparation of 1-n-butyl-2-methyl pyridinium bromide (2-MBPy)

A double surface reactor was equipped with a mechanical stirrer, a thermocouple well and two dropping funnels. The reactor was charged with 2-picoline (250 g) and heated to 85-90° C. n-butyl bromide (358.8 g) was added drop-wise during hours. DIW was added in small portions (15 ml in total). During feeding the temperature rose to 92-104° C. After feeding was completed the reaction mixture was heated for 3 hours (105° C.). DIW (100 ml) was added. The mixture was withdrawn from the reactor, and was evaporated using a rotavapor. Additional DIW (100 g) was added and the mixture was re-evaporated. DIW was added for dilution. Final product: 666 g, 81 weight % (argentometric titration); 89% yield.

Preparation 3

Preparation of 1-n-butyl-2-methyl pyridinium bromide (2-MBPy)

A double surface reactor was equipped with a mechanical stirrer, a condenser, a thermocouple well and a dropping funnel. The reactor was charged with 2-picoline (341 g) and acetonitrile (374 g) and heated to 78° C. n-butyl bromide (528 g) was added drop-wise during 2.5 hours. The reaction mixture was kept at 78-79° C. for 4 hours. The mixture was cooled and the solvent evaporated using a rotavapor. DIW (150 ml) was added and another evaporation was applied. Finally, the mixture was diluted with DIW. Final product: 559 g, 81% w; 54% yield.

The invention claimed is:

1. An electrolyte solution suitable for use in a zinc-bromine battery, comprising zinc bromide and a liquid complex composed of 1-n-butyl-2-methyl-pyridinium bromide combined with one or more bromine molecules.

2. A method of operating a zinc-bromine battery, the method comprising adding the electrolyte solution of claim 1 to an electrolyte of the zinc-bromine battery, and operating the zinc-bromide battery at a temperature above 30° C.

* * * * *